(12) United States Patent
Kalindjian et al.

(10) Patent No.: US 6,407,132 B1
(45) Date of Patent: Jun. 18, 2002

(54) SUBSTITUTED IMIDAZOLE DERIVATIVES AND THEIR USE AS HISTAMINE $H_3$ RECEPTOR LIGANDS

(75) Inventors: Sarkis Barret Kalindjian, Ban Stead; Ildiko Maria Buck, London, both of (GB)

(73) Assignee: James Black Foundation Limited, London (GB)

( * ) Notice: Subject to any disclaimer, the term of this patent is extended or adjusted under 35 U.S.C. 154(b) by 0 days.

(21) Appl. No.: 09/463,445

(22) PCT Filed: Jul. 14, 1990

(86) PCT No.: PCT/GB98/02063

§ 371 (c)(1),
(2), (4) Date: Mar. 13, 2000

(87) PCT Pub. No.: WO99/05115

PCT Pub. Date: Feb. 4, 1999

(30) Foreign Application Priority Data

Jul. 25, 1997 (GB) ............................................. 9715815

(51) Int. Cl.[7] ................ A61K 31/4164; A61K 31/4174; C07D 233/64

(52) U.S. Cl. .................. 514/400; 548/339.5; 548/340.1

(58) Field of Search ............................ 548/340.1, 339.5; 514/400

(56) References Cited

U.S. PATENT DOCUMENTS

| | | | |
|---|---|---|---|
| 4,988,689 A | 1/1991 | Janssens et al. | 514/212 |
| 5,217,986 A | 6/1993 | Pomponi et al. | 514/400 |
| 5,952,362 A | * 9/1999 | Cournoyer et al. | 514/398 |

FOREIGN PATENT DOCUMENTS

| | | |
|---|---|---|
| EP | 0 197 840 | 10/1986 |
| EP | 0 214 058 | 3/1987 |
| EP | 0 458 661 A1 | 11/1991 |
| EP | 0 494 010 A1 | 7/1992 |
| EP | 0 531 219 A1 | 3/1993 |
| WO | WO 91/17146 | 11/1991 |
| WO | WO 92/15567 | 9/1992 |
| WO | WO 93/01812 | 2/1993 |
| WO | WO 93/12093 | 6/1993 |
| WO | WO 93/12107 | 6/1993 |
| WO | WO 93/12108 | 6/1993 |
| WO | WO 93/14070 | 7/1993 |
| WO | WO 93/20061 | 10/1993 |
| WO | WO 94/17058 | 4/1994 |
| WO | WO/ 95/06037 | 3/1995 |
| WO | WO 95/11894 | 5/1995 |
| WO | WO 95/14007 | 5/1995 |

* cited by examiner

*Primary Examiner*—Laura L. Stockton
(74) *Attorney, Agent, or Firm*—Foley & Lardner

(57) ABSTRACT

Compounds of formula (I) and their pharmaceutically acceptable salts are useful as histamine $H_3$ receptor ligands. $R^1$ and $R^3$ are optional substituents such as $C_1$ to $C_6$ alkyl. $R^2$ represents a bond or $C_1$ to $C_5$ (preferably $C_1$ to $C_3$) hydrocarbylene; $R^4$ represents a bond or $C_1$ to $C_5$ (preferably $C_1$ to $C_3$) hydrocarbylene; $R^5$ is hydrogen, $C_1$ to $C_3$ alkyl, $R^8$—O—($C_1$ to $C_3$)alkyl (wherein $R^8$ is hydrogen or $C_1$ to $C_3$ alkyl), aryl, aryl($C_1$ to $C_3$)alkyl; $R^6$ represents a bond or —$NR^9$—, wherein $R^9$ is any of the groups mentioned above for $R^5$; $R^7$ is H or $C_1$ to $C_{15}$ hydrocarbyl (in which one or more hydrogen atoms may be replaced by halogen, and up to three carbon atoms may be replaced by oxygen, nitrogen or sulfur atoms); a is from 0 to 2; and b is from 0 to 3.

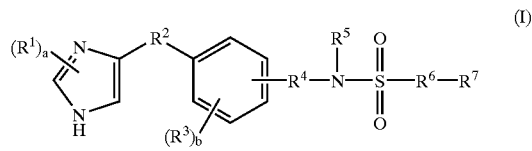

17 Claims, 6 Drawing Sheets

SUBSTITUTED IMIDAZOLE DERIVATIVES AND THEIR USE AS HISTAMINE $H_3$ RECEPTOR LIGANDS

This application is a 371 of PCT/GB98/02063 filed Jul. 14, 1998.

This invention relates to compounds which bind to histamine $H_3$ receptors, and to methods of making such compounds.

Histamine is well known as a mediator in certain hypersensitive reactions of the body, such as allergic rashes, hayfever and asthma. These conditions are now commonly treated with potent antagonists of histamine, so-called "antihistamines".

In the 1940s, it was noted that some physiological effects of histamine, such as increased gastric acid secretion and cardiac stimulation, were not blocked by the antihistamines which were then available. This led to the proposal that histamine receptors exist in at least two distinct types, referred to as $H_1$ and $H_2$ receptors. Subsequently, $H_2$ antagonists (such as cimetidine, ranitidine and famotidine) were identified and they have become important in the treatment of gastric ulcers.

In the early 1980s, it was established that histamine also has a role as a neurotransmitter in the central nervous system. Arrang et al., Nature 302, 832 to 837 (1983), proposed the existence of a third histamine receptor subtype ($H_3$) located presynaptically on histaminergic nerve endings. Arrang et al. postulated that the $H_3$ receptor is involved in inhibiting the synthesis and release of histamine in a negative feedback mechanism The existence of the $H_3$ receptor was subsequently confirmed by the development of selective $H_3$ agonists and antagonists (Arrang et al., Nature 327, 117 to 123 (1987)). The $H_3$ receptor has subsequently been shown to regulate the release of other neurotransmitters both in the central nervous system and in peripheral organs, in particular in the lungs and GI tract. In addition, $H_3$ receptors are reported to regulate the release of histamine from mast cells and enterochromaffinike cells.

A need exists for potent and selective $H_3$ ligands (both agonists and antagonists) as tools in the study of the role of histamine as a neurotransmitter, and in its roles as a neuro-, endo- and paracrine hormone. It has also been anticipated that $H_3$ ligands will have therapeutic utility for a number of indications including use as sedatives, sleep regulators, anticonvulsants, regulators of hypothalamo-hypophyseal secretion, antidepressants and modulators of cerebral circulation, and in the treatment of asthma and irritable bowel syndrome.

A number of imidazole derivatives have been proposed in the patent literature as $H_3$ ligands. Representative are the disclosures of EP-A-0197840, EP-A-0214058, EP-A-0458661, EP-A-0494010, EP-A-0531219, WO91/17146, WO92/15567, WO93/01812, WO93/12093, WO93/12107, WO93/12108, WO93/14070), WO93/20061, WO94/17058, WO95/06037, WO95/11894, WO95/14007, U.S. Pat. No. 4,988,689 and U.S. Pat. No. 5,217,986.

According to the present invention, there is provided a compound of the formula wherein
$R^1$ is selected from $C_1$ to $C_6$ alkyl, $C_1$ to $C_6$ alkoxy, $C_1$ to $C_6$ alkylthio, carboxy, carboxy($C_1$ to $C_6$)alkyl, formyl, $C_1$ to $C_6$ alklycarbonyl, $C_1$ to $C_6^-$ alkylcarbonylalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano;

$R^2$ represents a bond or $C_1$ to $C_5$ (preferably $C_1$ to $C_3$) hydrocarbylene;

$R^3$ is selected from the groups recited above for $R^1$, $R^4$ represents a bond or $C_1$ to $C_5$ (preferably $C_1$ to $C_3$) hydrocarbylene;

$R^5$ is hydrogen, $C_1$ to $C_3$ alkyl, or $R^8$—O—($C_1$ to $C_3$)alkyl (wherein $R^8$ is hydrogen or $C_1$ to $C_3$ alkyl), aryl, aryl($C_1$ to $C_3$)alkyl or heterocyclic($C_1$ to $C_3$)alkyl;

$R^6$ represents a bond or —$NR^9$—, wherein $R^9$ is any of the groups recited above for $R^5$;

$R^7$ is H or $C_1$ to $C_{15}$ hydrocarbyl (in which one or more hydrogen atoms may be replaced by halogen, and up to three carbon atoms may be replaced by oxygen, nitrogen or sulfur atoms, provided that $R^7$ does not contain an —O—O-group), a is from 0 to 2 (preferably 0); and b is from 0 to 3 (preferably 0);

and pharmaceutically acceptable salts thereof $R^5$ is preferably hydrogen, $C_1$ to $C_3$ alkyl, or $R^8$—O—($C_1$ to $C_3$)alkyl (wherein $R^8$ is hydrogen or $C_1$ to $C_3$ alkyl).

$R^9$ is preferably hydrogen, $C_1$ to $C_3$ alkyl, or $R^8$—O—($C_1$ to $C_3$)alkyl (wherein $R^8$ is hydrogen or $C_1$ to $C_3$alkyl).

$R^7$ is preferably hydrogen, cycloalkyl($C_1$ to $C_3$) alkyl, aryl or aryl($C_1$ to $C_3$)alkyl. Particularly preferred are compounds in which $R^7$ is phenyl, phenyl($C_1$ to $C_3$)alkyl, naphthyl or naphthyl($C_1$ to $C_3$)alkyl, optionally substituted by $C_1$ to $C_6$ alkyl, $C_1$ to $C_6$ alkoxy, $C^1$ to $C_6$alkylthio, carboxy, carboxy ($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, amino, $C_1$ to $C_6$ alkylamino, di($C_1$ to $C_6$ alkyl)amino, halo, sulfamoyl and cyano.

$R^2$ is preferably a bond or $C_1$ to $C_3$ hydrocarbylene.

$R^4$ is also preferably a bond or $C_1$ to $C_3$ hydrocarbylene.

The invention also comprehends derivative compounds ("pro-drugs") which are degraded in vivo to yield the species of formula (1). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, pp. 112–176 (1985), and *Drugs*, 29, pp.455–473 (1985).

Pro-drug forms of the pharmacologically-active compounds of the invention will generally be compounds according to formula (I) having an acid group which is esterified or amidated. Included in such esterified acid groups are groups of the form —COOR$^{10}$, wherein R$^{10}$ is C$_1$ to C$_5$ alkyl, phenyl, substituted phenyl, benzyl, substituted benzyl, or one of the following:

Amidated acid groups include groups of the formula —CONR$^{11}$R$^{12}$, wherein R$^{11}$ is H, C$_1$ to C$_5$ alkyl, phenyl, substituted phenyl, benzyl, or substituted benzyl, and R$^{12}$ is —OH or one of the groups just recited for R$^{11}$.

Compounds of formula (I) having an amino group may be derivatised with a ketone or an aldehyde such as formaldehyde to form a Mannich base. This will hydrolyse with first order kinetics in aqueous solution.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

The compounds of the invention may exist in various enantiomeric, diastereomeric and tautomeric forms. It will be understood that the invention comprehends the different enantiomers, diastereomers and tautomers in isolation from each other, as well as mixtures of enantiomers, diastereomers and tautomers.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups. The term "hydrocarbylene" refers to corresponding divalent groups, the two free valencies being on separate atoms.

When reference is made herein to a carbon atom of a hydrocarbyl group being replaced by O, S or N, it will be understood that what is meant is that a —CH$_2$— group is replaced by —O— or —S—, or that is replaced by A "carbocyclic" group, as the term is used herein, comprises one or more closed chains or rings, which consist entirely of carbon atoms, and which may be substituted. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above, which may be substituted.

A "heterocyclic" group comprises one or more closed chains or rings which have at least one atom other than carbon in the closed chain or ring, and which may be substituted. Examples include benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

When reference is made herein to a substituted carbocyclic group (such as substituted phenyl) or a substituted heterocyclic group, the substituents are preferably from 1 to 3 in number and selected from C$_1$ to C$_6$ alkyl, C$_1$ to C$_6$ alkoxy, C$_1$ to C$_6$ alkylthio, carboxy, carboxy(C$_1$ to C$_6$)alkyl, formyl, C$_1$ to C$_6$ alkylcarbonyl, C$_1$ to C$_6$ alkylcarbonylalkoxy, nitro, trihalomethyl, hydroxy, amino, C$_1$ to C$_6$ alkylamino, di(C$_1$ to C$_6$ alkyl)amino, aryl, C$_1$ to C$_6$ alkylaryl, halo, sulfamoyl and cyano.

The term "halogen", as used herein, refers to any of fluorine, chlorine, bromine and iodine.

We have found that a number of compounds in the prior art have shown a significant discrepancy in their activity as measured by two ileum based assays which are described below. We would interpret discrepancies between the functional and binding assays of greater than about 0.5 log units as significant. Analysis of data obtained in these particular functional and radioligand binding assays and also in other related bioassays suggests that the discrepancy may be connected, at least in part, with residual efficacy inherent in these structures. In practice, this means that these particular compounds may act as agonists, at least in some tissues.

Surprisingly, we have found that the compounds disclosed herein do not show a significant discrepancy in the two assays. Thus, these compounds may be considered to have minimal potential to express agonist action, and would be expected to behave as antagonists or, at constitutively-active receptors, as inverse agonists. In one aspect, therefore, the present invention provides the use of these compounds as histamine antagonists or inverse agonists, and in the manufacture of medicaments for this purpose.

Pharmaceutically acceptable salts of the acidic or basic compounds of the invention can of course be made by conventional procedures, such as by reacting the free base or acid with at least a stoichiometric amount of the desired salt-forming acid or base.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as anaqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will Generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 μg/kg and 50 mg/kg, especially between 10 μg/kg and 10 mg/kg, eg. between 100 μg/kg and 2 mg/kg.

BRIEF DESCRIPTION OF DRAWINGS

Figure 1:
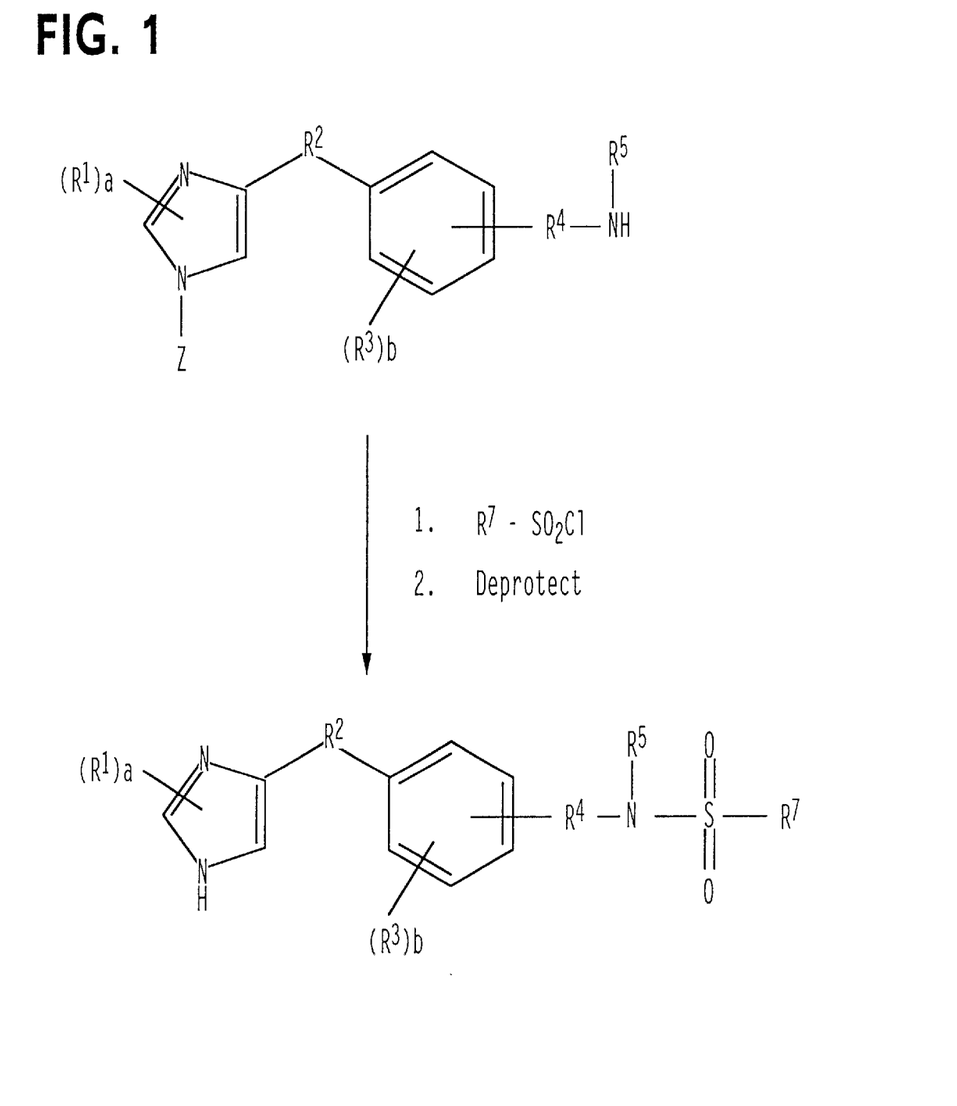

Compounds of the invention can conveniently be prepared from amines of the formula (II)

in which Z represents a suitable protecting group. For example, compounds in which $R^6$ is a bond may be prepared by reacting an amine of formula II with a sulfonyl chloride of the formula $R^7SO_2Cl$, followed by deprotection, as illustrated in FIG. 1.

Figure 2:
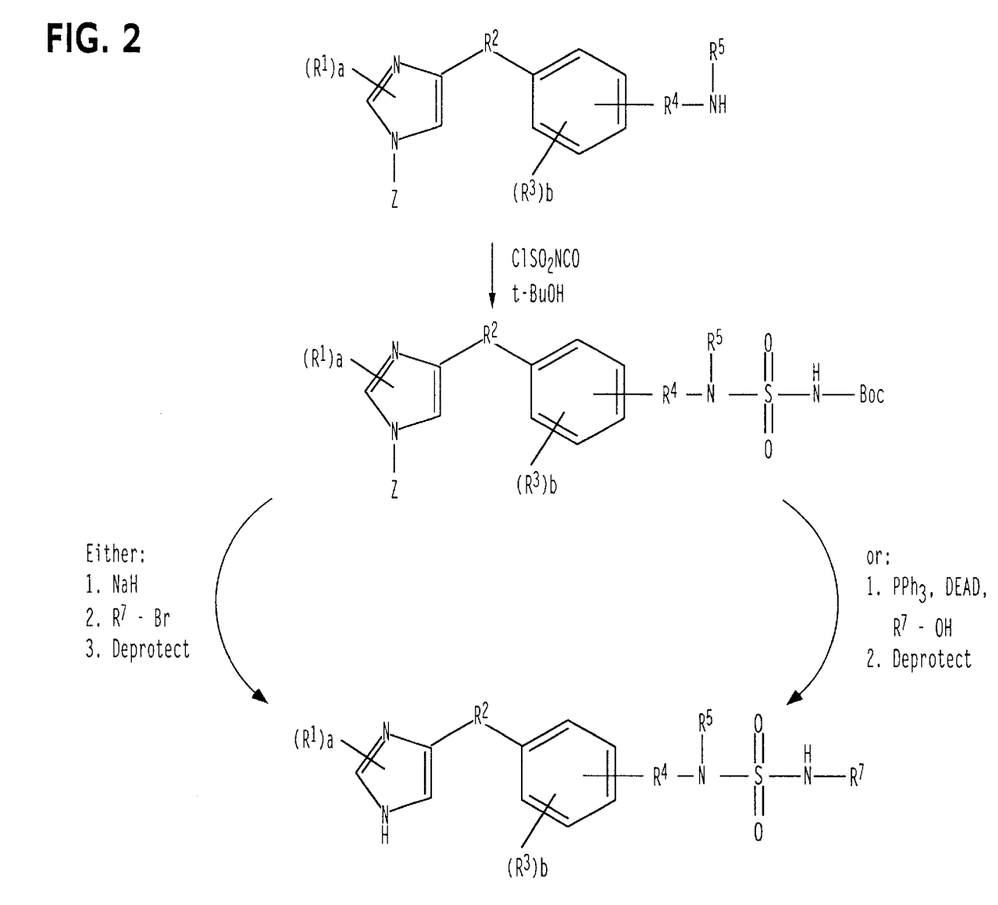

Compounds of formula I in which $R^6$ is —NH— can be prepared from amines of formula II by either of the two routes illustrated in FIG. 2.

Figure 3:
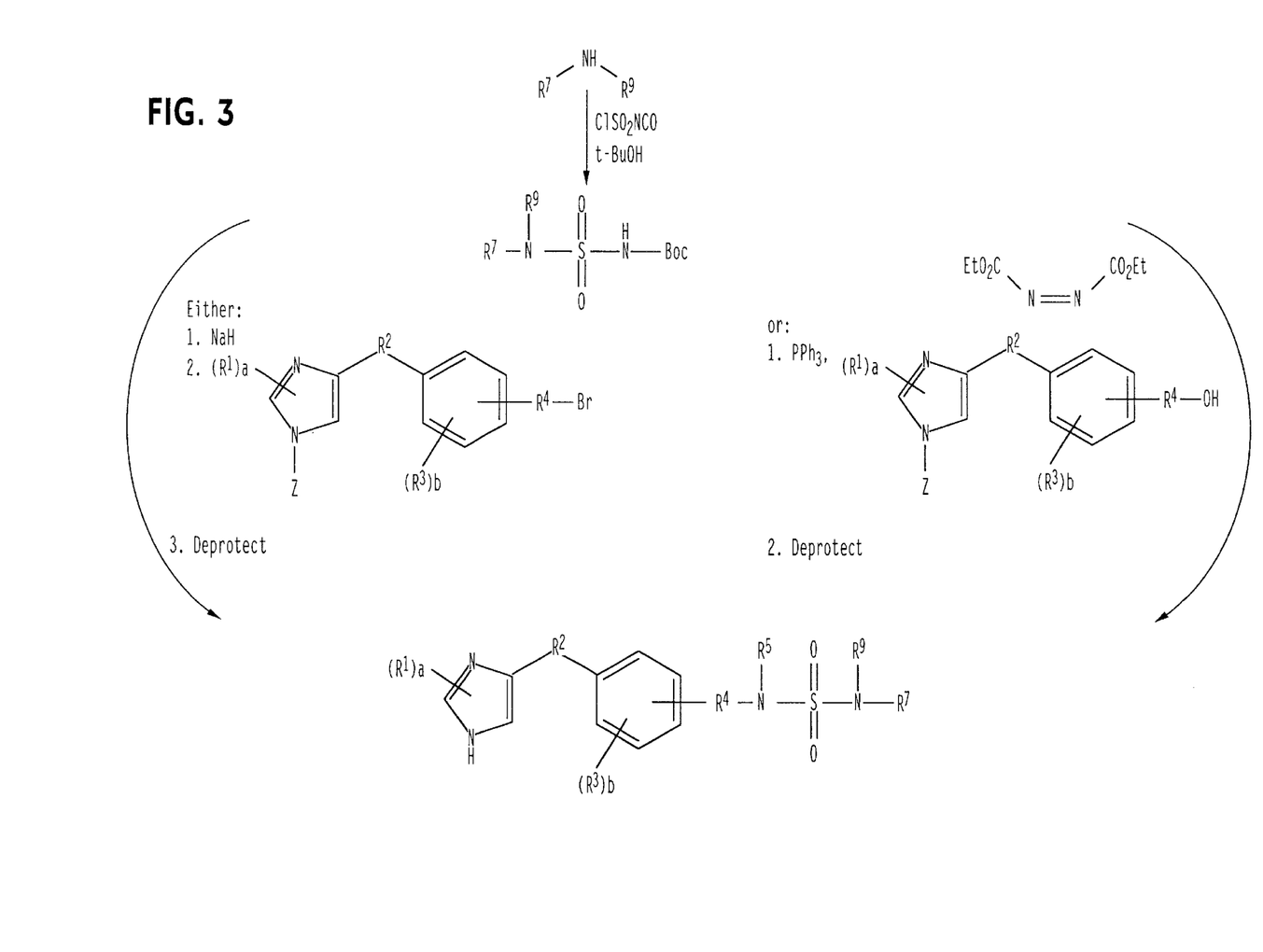
Figure 4:
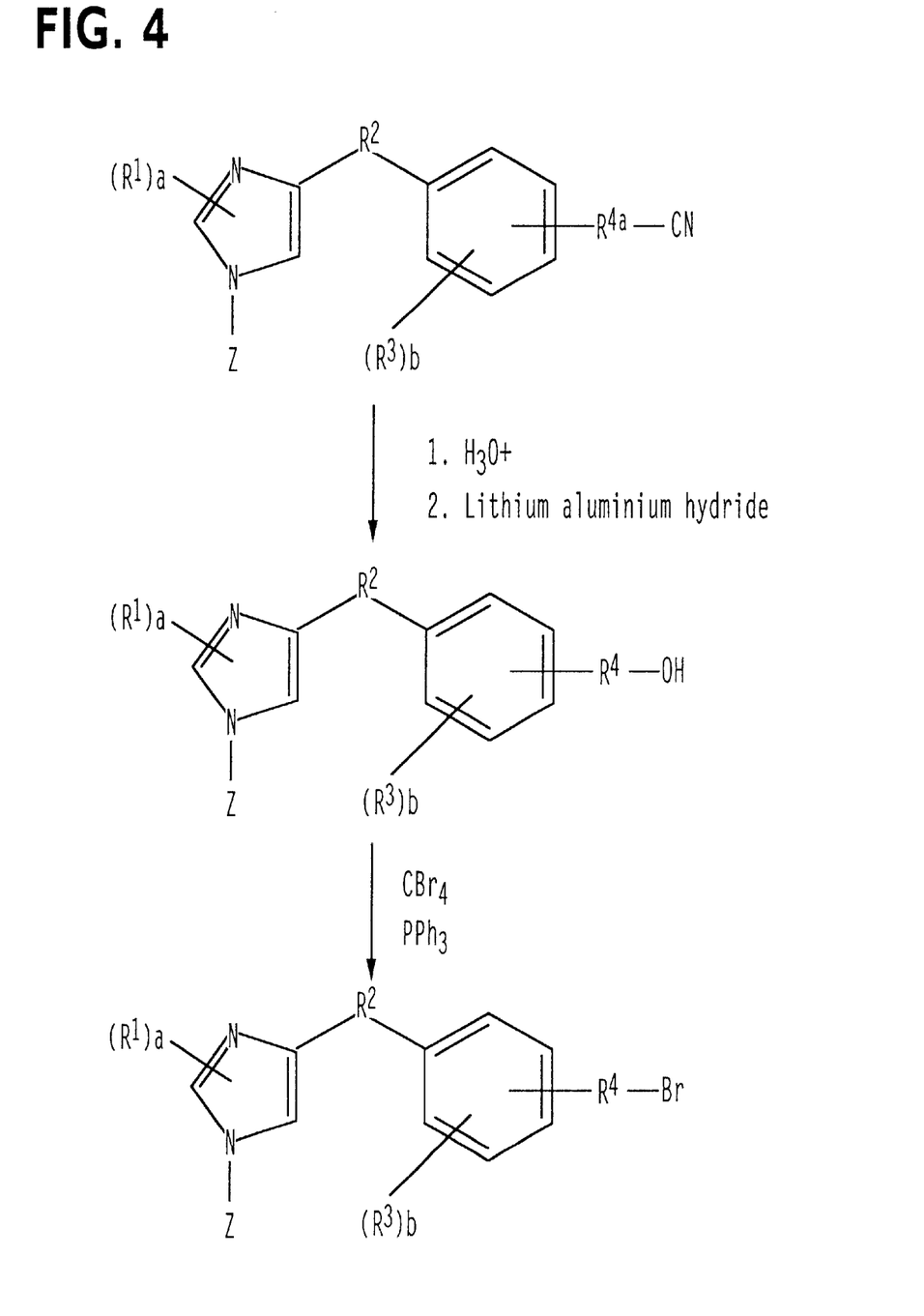

In an alternative approach, compounds in which $R^6$ is —$NR^9$— can be prepared starting with an amine of the formula $R^7$—NH—$R^9$, as illustrated in FIG. 3. As shown in this Figure, either of two different routes can be followed, using intermediates of the formula FIG. 4 illustrates the preparation of these intermediates. In FIG. 4, $R^{4a}$ is $C_1$ to $C_4$ hydrocarbylene.

Figure 5A:
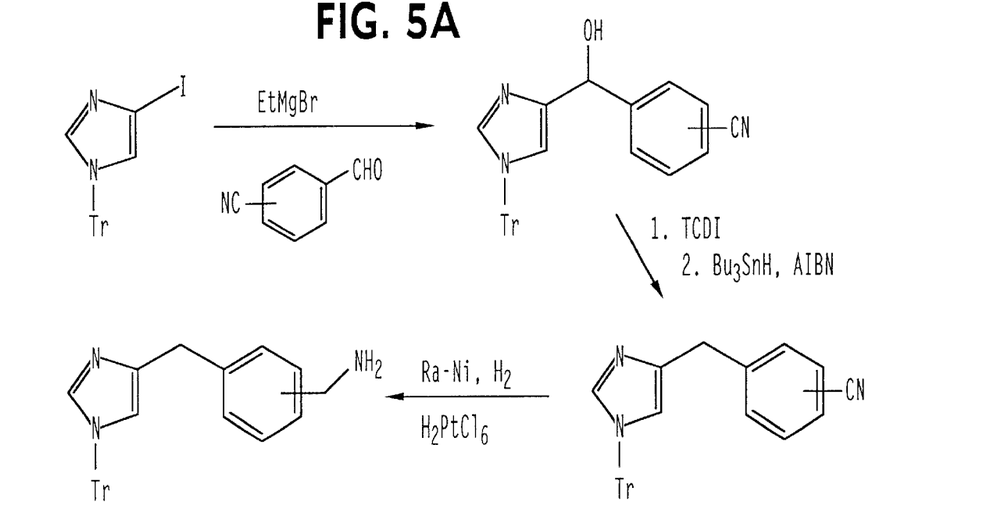
Figure 5B:
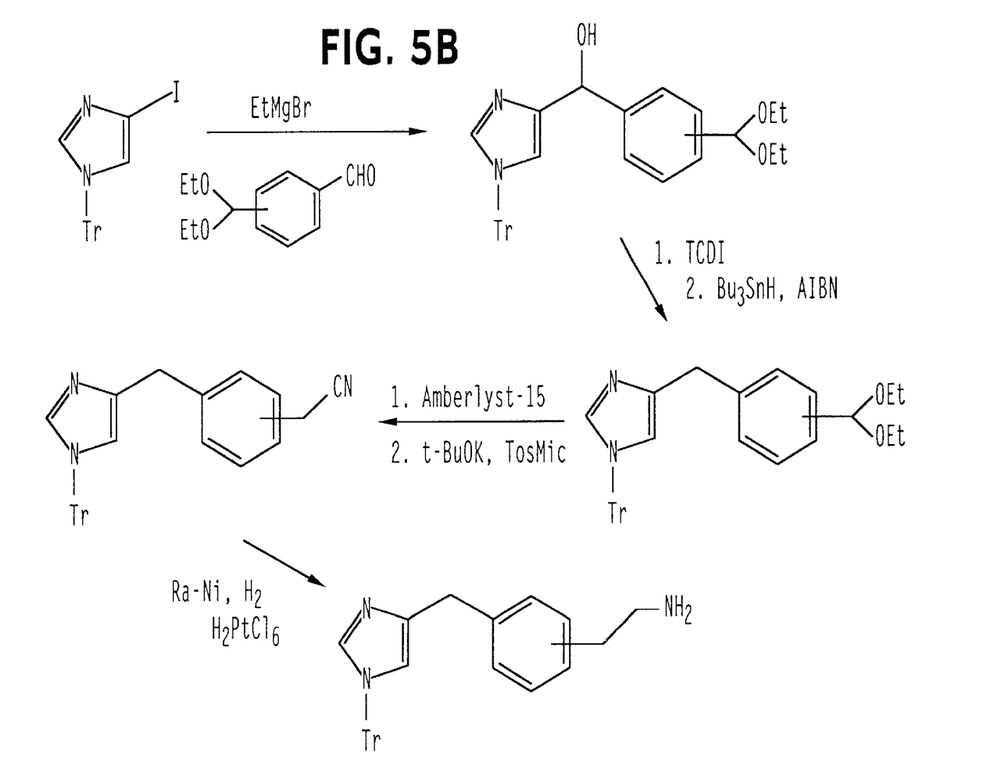

Amines of formula II in which $R^4$ is a hydrocarbylene group can conveniently be prepared by methods such as those illustrated in FIGS. 5A and 5B, in which Tr represents a trityl group. It will be understood that other protecting groups may be used instead of trityl.

Figure 6:
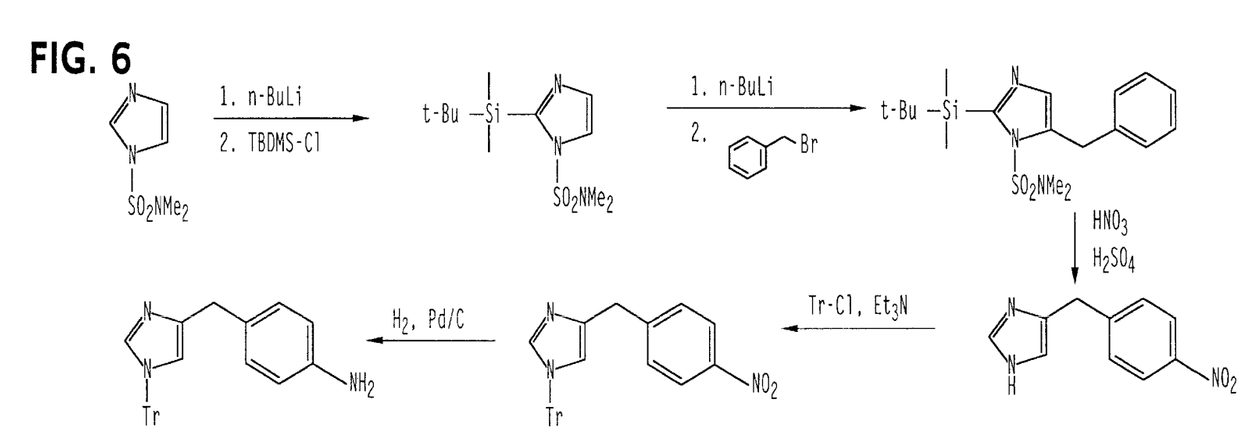
Figure 7:
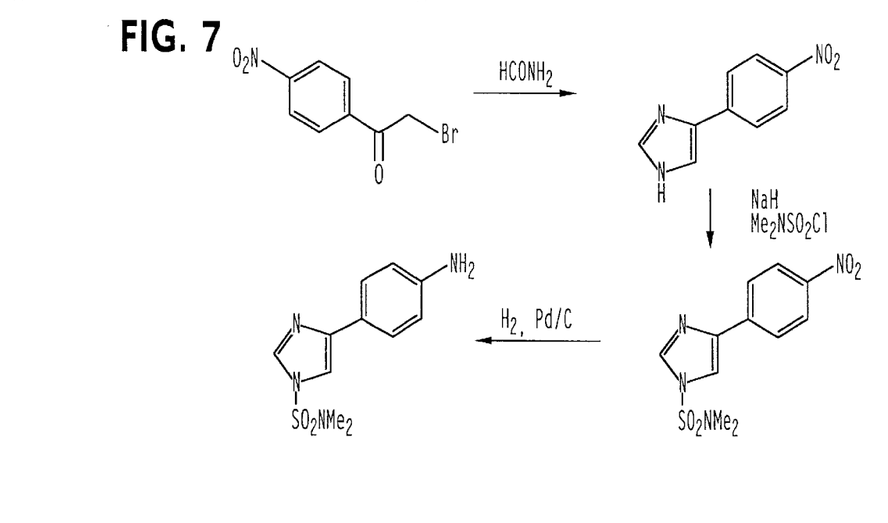

Amines of formula II in which $R^4$ is a bond can conveniently be prepared by a method such as that illustrated in FIG. 6, while those in which $R^2$ is a bond may be obtained by the method shown in FIG. 7.

The invention is now further illustrated by means of the following examples.

EXAMPLE 1

Naphthalene-2-sulfonic Acid [4(1H-Imidazol-4-ylmethyl)-phenyl]-amide

Step a. 4-[Hydroxy-(1-trityl-1H-imidazol-4-yl)-methyl]-benzonitrile. 4-Iodo-1-trityl-imidazole (synthesized according to the references given in reference 1;6.50 g, 15.0 mmol) was dissolved in dry dichloromethane (65 ml), cooled to 0° C. under argon and a solution of ethyl magnesium bromide in ether (5.5 ml of a 3M solution; 16.5 mmol ) was added dropwise. The reaction was stirred at room temperature for 30 minutes and the solution of 4-cyanobenzaldehyde (2.00 g, 15.0 mmol) in dry dichloromethane (10 ml) was slowly added. The reaction was stirred overnight and then quenched by the addition of saturated ammonium chloride solution (80 ml). The organic layer was separated and the aqueous layer was extracted with additional dichloromethane (2×50 ml). The combined organic layers were dried ($MgSO_4$) and concentrated to give a white solid (6.80 g) which was triturated with dichloromethane (30 ml) to afford 5.00 g of the product. The mother liquid was evaporated to half of its volume to yield a further 0.5 g of product. $^1H$ NMR (300 MHz, $CDCl_3$) 7.58 (2H, d), 7.52 (2H, d), 7.41 (1H, s), 7.32 (9H, m), 7.10 (6H, m), 6.57 (1H, s), 5.79 (1H, s), 4.00 (1H, br s).

Step b. 4-(1-imityl-1H-imidazol-4-ylmethyl)-benzonitrile. A suspension of the product from step a (4.00 g, 9.10 mmol) and thiocarbonyldiimidazole (TCDI) (2.40 g, 13.5 mmol) was heated to reflux in tetrahydrofuran (100 ml) under argon. After 2 h additional thiocarbonyldiimidazole (0.60 g) was added and the reaction was stirred at room temperature overnight. The solvent was evaporated, the residue dissolved in dichloromethane (100 ml) and washed with saturated ammonium chloride solution. The aqueous phase was extracted with additional dichloromethane (2×50 ml). The combined organic layers were washed with water and brine, dried (MgSO$_4$) and evaporated. Flash column chromatography (silica; hexane:ethyl acetate 20:80) of the residue afforded the thioimidazolide (4.30 g) as a yellow foam. A solution of the thioimidazolide (4.30 g, 7.80 mmol) and catalytic 2,2'-azobisisobutyronitrile (AIBN, 0.2 g) in dry toluene (100 ml) was slowly added to a solution of tributyltin hydride (4.7 ml, 17.4 mmol) in refluxing dry toluene (100 ml) under an argon atmosphere. Additional AIBN (0.08 g) and tributyltin hydride (1.3 ml, 4.80 mmol) were added and the reaction was stirred at reflux overnight. After cooling to room temperature carbon tetrachloride (10 ml) was added and the stirring was continued for 1 h. The reaction mixture was diluted with diethyl ether (100 ml), 1,8-diazabicyclo[5.4.0]undec-7-ene (DBU, 3.6 ml, 24.1 mmol) was added then 0.1 M solution of iodine in diethyl ether until the iodine colour persisted. The mixture was filtered through a plug of silica, the filtrate was evaporated and the residue was triturated with hexane:isopropanol 85:15 (20 ml) to afford white solid (2.10 g).

$^1$H NMR (300 MHz, CDCl$_3$) 7.55 (2H, d), 7.39 (1H, s), 7.34 (11H, m), 7.13 (6H, m), 6.59 (1H, s), 3.94 (2H, s).

Step c. 4-(1-Trityl-1H-imidazol-4-ylmethyl)-benzylamine. The product of step b (1.60 g, 3.80 mmol) was suspended in methanol saturated with ammonia (50 ml). Raney-Nickel (ca. 1 g) and chloroplatinic acid (80 mg dissolved in 1 ml of water) were added. The mixture was stirred in a Parr bottle under H$_2$ pressure (about 40 psi) for 24 h. The reaction mixture was filtered through Celite and the filtrate was evaporated. The crude material was purified by flash column chromatography (silica; dichloromethane:methanol:ammonia (880) 95:5:0.5) to afford the product as a white solid (1.44 g). $^1$H NMR (300 MHz, CDCl$_3$) 7.35 (10H, m), 7.20 (4H, m), 7.14 (6H, m), 6.56 (1H, s), 3.88 (2H, s), 3.82 (2H, s), 2.36 (2H, br s)

Step d. Naphthalene-2-sulfonic acid [4-(1-trityl-1H-imidazol-4-ylmethyl)-phenyl]-amide. The product of step c (0.11 g, 0.26 mmol) was dissolved in dry dichloromethane (3 ml) and the solution was cooled to 0° C. under argon. Triethylamine (0.05 ml, 0.34 mmol), then 2-naphthalenesulfonyl chloride (60 mg, 0.26 mmol) were added and the mixture was stirred at room temperature overnight, diluted with dichloromethane (10 ml) and washed with saturated sodium bicarbonate solution (2×10 ml). The organic phase was dried and evaporated. The crude product was purified by flash column chromatography (silica; dichloromethane:ethyl acetate 80:20) to afford the product as a colourless foam (0.13 g). $^1$H NMR (300 MHz, CDCl$_3$) 8.44 (1H, s), 7.95 (3H, m), 7.84 (1H, m), 7.63 (2H, m), 7.33 (11H, m), 7.12 (9H, m), 6.52 (1H, s), 4.68 (1H, t), 4.12 (2H, s), 3.81 (2H, s).

Step e. A solution of the product from step d (0.13 g, 0.21 mmol) in a mixture of ethanol (3 ml) and 1M hydrochloric acid (0.5 ml) was heated at reflux overnight, then the solvent was removed in vacuo. Flash column chromatography (silica, dichloromethane:methanol:ammonia (880) 90:10:1) of the residue afforded the title compound as a white solid (58.5 mg). $^1$H NMR (300 MHz, CDCl$_3$) 8.44 (1H, s), 7.86 (4H, m), 7.66 (2H, m), 7.59 (1H, s), 7.09 (4H, s), 6.69 (1H, s), 4.20 (1H, br s), 4.12 (2H, s), 3.85 (2H, s). The maleate salt was prepared by lyophilisation of an equimolar solution of the product and maleic acid in water/dioxan. Found C 58.37, H 4.90, N 7.78%, C$_{25}$H$_{23}$N$_3$O$_6$S.1.3 H$_2$O requires C 58.08, H 4.99, N 8.13%

EXAMPLE 2

C-(4-Chlorophenyl)-N-[4-(1H-imidazol-4-ylmethyl)-benzyl]-methanesulfonamide

Step a. C-(4-Chloro-phenyl)-N-[4-(1-trityl-1H-imidazol-4-ylmethyl)-benzyl]-methanesulfonamide. To a solution of the product from example 1 step c (0.32 g, 0.74 mmol) and triethylamine (0.12 ml, 0.88 mmol) in dry dichloromethane (10 ml), cooled under an atmosphere of argon to −78° C., was added dropwise a solution of (4-chlorophenyl)methanesulfonyl chloride (0.2 g, 0.88 mmol) in dry dichloromethane (3 ml). The resultant solution was stirred for 18 h, allowed to warm to room temperature and then diluted with dichloromethane, washed with water (2×20ml), and the combined organic layers dried and evaporated. Flash column chromatography (silica; dichloromethane:methanol 95:5) of the residue afforded the product as a colourless oil (0.32 g). $^1$H NMR (300 MHz, CDCl$_3$) 7.32–7.10 (24H, m), 6.55 (1H, s), 4.41 (1H, t), 4.13 (4H, m), 3.89 (2H, s).

Step b. A solution of the product from step a (0.31 g, 0.50 mmol) in a mixture of ethanol (10 ml) and 1M hydrochloric acid (1.5 ml) was heated at reflux for 4h, then the solvent was removed in vacuo. The residue was triturated with diethyl ether to afford the the hydrochloride salt of the title compound (0.18 g). $^1$H NMR (300 MHz, d$_6$-DMSO) 14.43 (2H, br s), 8.99 (1H, s), 7.67 (1H, t), 7.41 (3H, m), 7.32 (2H, m), 7.25 (4H, s), 4.33 (2H, s), 4.06 (2H, d), 4.01 (2H, s). Found C 52.02, H 4.72, N 10.07%, C$_{18}$H$_{19}$Cl$_2$N$_3$O$_2$S requires C 52.43, H 4.64, N 10.19%.

EXAMPLE 3

N-(4-Chloro-benzyl)-N'-[4-(1H-imidazol-4-ylmethyl)-benzyl]-sulfamide

Step a. N-tert-Butoxycarbonyl-N'-[4-(1-trityl-1H-imidazol-4-ylmethyl)-benzyl]-sulfamide. To a solution of chlorosulfonyl isocyanate (0.27 ml, 3.2 mmol) in dry dichloromethane (5 ml), cooled in ice under an atmosphere of argon, was added dropwise a solution of dry tert-butanol (0.45 ml, 4.80 mmol) in dry dichloromethane (3 ml). The solution was allowed to warm to room temperature, stirred for 10 min and added dropwise, under argon, to an ice cooled solution of the product of example 1 step c (1.06 g, 2.50 mmol) and triethylamine (0.52 ml, 3.70 mmol) in dry dichloromethane (10 ml). The mixture was stirred for 18 h, allowed to warm to room temperature and then diluted with dichloromethane, washed with water (2×20 ml), and the combined organic layers dried and evaporated. Flash column chromatography (silica; dichloromethane:methanol:ammonia (880) 90:10:1) of the residue afforded the product as a colourless oil (1.40 g). $^1$H NMR (300 MHz, CDCl$_3$) 7.44 (1H, s), 7.34 (9H, m), 7.15 (10H, m), 6.60 (1H, s), 5.10 (1H, br s), 3.92 (4H, m), 3.49 (1H, s), 1.44 (9H, s).

Step b. N-tert-Butoxycarbonyl-N-(4-chloro-benzyl)-N'-[4-(1-trityl-1H-imidazol-4-ylmethyl)-benzyl]-sulfamide. To a solution of the product from step a (0.61 g, 1.00 mmol) and 4-chlorobenzyl bromide (0.21 g, 1.00 mmol) in dry N,N-dimethyiformamide (5 ml), cooled to 0° C. under an atmosphere of argon, was added sodium hydride (54 mg, 1.20 mmol, 60% dispersion in oil). The mixture was stirred for 18 h and allowed to warm slowly to room temperature. Water (20 ml) was added and the mixture was extracted with ethyl acetate (2×20 ml). The combined organic extracts were washed with water, dried over magnesium sulfate and evaporated. Flash column chromatography (silica; dichloromethane:ethyl acetate 90:10) of the residue afforded the product (0.34 g). $^1$H NMR (300 WHz, CDCl$_3$) 7.37–7.11 (24H, m), 6.56 (1H, s), 5.50 (1H, t), 4.72 (2H, s), 3.97 (2H, d), 3.88 (2H, s), 1.42 (9H, s).

Step c. A solution of the product from step b (0.13 g, 0.18 mmol) in a mixture of ethanol (5 ml) and 1M hydrochloric acid (1.0 ml) was heated at reflux for 4 h, then the solvent was removed in vacuo. The residue was triturated with diethyl ether to afford the title compound as the hydrochloride salt (65 mg). $^1$H NMR (300 MHz, d$_6$-DMSO) 8.94 (1H, s), 8.50 (1H, br s), 7.50–7.21 (10H, m), 3.98 (6H, m). Found C 48.26, H 4.94, N 12.29%, C$_{18}$H$_{20}$Cl$_2$N$_4$O$_2$S requires C48.12, H5.03, N 12.47%.

EXAMPLE 4

C-(4-Chloro-phenyl)-N-[4-(1H-imidazol-4-ylmelhyl)-phenyl]-methanesulfonamide

Step a. 2-(tert-Butyl-dimethylsilyl)-1-(N,N-dimeihylsulfamoyl)-1H-imidazole. A solution of 1-(N,N-dimethylsulfamoyl)-imidazole$^2$ (4.48 g, 25.6 mmol) in dry tetrahydrofuran (100 ml) was cooled under an atmosphere of argon to −78° C. n-Butyl lithium (1.5M in hexanes) (18.0 ml, 27.0 mmol) was added over 30 min and the solution stirred for a further 30 min. To the resulting brown solution was added over 15 min a solution of tert-butyldimethylsilyl chloride (4.37 g, 28.2 mmol) in dry tetrahydrofuran (20 ml). The solution was allowed to warm to room temperature and stirred for 24 h. Saturated ammonium chloride solution (100 ml) and diethyl ether (100 ml) were added and the ethereal extract was washed with brine and dried over magnesium sulfate. Filtration and evaporation of the filtrate gave an oily residue, which was purified by flash column chromatography (silica; ethyl acetate) to afford the product as an amber solid (6.97 g).

Step b. 5-Benzyl-2-(tert-butyl-dimethylsilyl)-1-(N,N-dimethylsulfamoyl)-1H-imidazole. A solution of the product from step a (5.00 g, 18.20 mmol) in dry tetrahydrofuran (100 ml) was cooled under an atmosphere of argon to −78° C. n-Butyl lithium (1.6M in hexanes) (11.4 ml, 18.20 mmol) was added over 15 min and the solution stirred for a further 30 min. A solution of benzyl bromide (2.16 ml, 18.20 mmol) in dry. tetrahydrofuran (20 ml) was added over 10 min. The solution was stirred for 1 h and allowed to warm to room temperature. Saturated ammonium chloride solution (100 ml) and ethyl acetate (100 ml) were added and the organic extract was washed with brine and dried over sodium sulfate. Filtration, evaporation of the filtrate and purification by flash column chromatography (silica, dichloromethane) afforded the product as a pale yellow foam (3.73 g). $^1$H NMR (300 MHz, CDCl$_3$) 7.35–7.17 (5H, m), 6.73 (1H, s), 4.11 (2H, s), 2.68 (6H, s), 1.03 (9H, s), 0.40 (6H, s).

Step c. 4-(4-Nitro-benzyl)-1H-imidazole. The product of step b was heated at reflux in 10% nitric acid (30 ml) for 3 h. The solution was cooled to room temperature and washed with ethyl acetate (2×30 ml). The aqueous phase was evaporated in vacuo and dried under high vacuum overnight. The nitrate salt was added to concentrated sulfuric acid (5 ml) then heated to 100° C. for 2 h. The mixture was diluted with water (40 ml), neutralized with sodium hydroxide and then sodium carbonate at 60° C. After cooling to ambient temperature the product was extracted with dichloromethane (2×20 ml), the organic phase was dried (magnesium sulfate) and evaporated. The crude product was purified by flash colunm chromatography (silica; dichloromethane:methanol 95:5), then crystallization from dichloromethane:diethyl ether to afford the title compound as a beige solid (0.53 g). $^1$H NMR (300 MHz, d$_6$-DMSO) 11.95 (1H, s), 8.13 (2H, d), 7.54 (1H, s), 7.49 (2H, d), 6.84 (1H, s), 3.97 (2H, s).

Step d. 4-(4-Nitro-benzyl)-1-trityl-1-imidazole. To a solution of the product from step c (0.50 g, 2.46 mmol) in dry dichloromethane (20 ml) were added triethylamine (0.40 ml, 3.00 mmol) and triphenylmethyl chloride (0.69 g, 2.46 mmol). The solution was stirred for 18 h, washed with water (3×10 ml), dried over magnesium sulfate and the solvent was evaporated in vacuo. The crude product was crystallised from dichloromethane:diethyl ether 10:90 to afford a beige solid (0.92 g). $^1$H NMR (300 MHz, CDCl$_3$) 8.13 (2H, d), 7.54 (1H, s), 7.41 (2H, d), 7.38–7.09 (15H, m), 6.63 (1H, s), 4.04 (2H, s).

Step e. 4-(1-Trityl-1H-imidazol-4-ylmethyl)-phenylamine. A round bottom flask containing the product from the previous step (0.90 g, 2.02 mmol), 10% palladium-on-charcoal (90 mg) and THF (50 ml) was evacuated and flushed with hydrogen three times. The mixture was vigorously stirred overnight under an atmosphere of hydrogen. The catalyst was removed by filtration and the filtrate evaporated to afford yellow solid (0.82 g): $^1$H NMR (300 MHz, CDCl$_3$) 7.47 (1H, s), 7.35–7.10 (15H, m), 7.02 (2H, d), 6.60 (2H, d), 6.51 (1H, s), 3.83 (2H, s), 3.30 (2H, br s).

Step f. C-(4-Chloro-phenyl)-N-[4-(1-trityl-1-imidazol-4-ylmethyl)-phenyl]-methanesulfonamide. The product was prepared according to the procedure given in Example 2 step a using the product of step e above instead of the product of Example 1 step c as the substrate. $^1$H NMR (300 MHz, CDCl$_3$) 7.37–7.00 (25H, m), 6.58 (1H, s), 4.24 (2I, s), 3.87 (2H, s).

Step g. The product from the previous step was converted to the hydrochloride salt of the title compound using the procedure given in Example 2 step b. $^1$H NMR (300 MHz, d$_6$-DMSO) 14.40 (1H, br s), 9.84 (1H, s), 9.02 (1H, s), 7.27 (10H, m), 4.46 (2H, s), 3.98 (2H, s).

EXAMPLE 5

C-(4-Chloro-phenyl)-N-[4-(1H-imidazol-4-yl)-pheriyl]-methanesulfonamide

Step a. 4-(4-Nitro-phenyl)-1-imidazole. 2-Bromo4'-nitroacetophenone (2.44 g, 10.0 mmol) in dry formamide (10 ml) was heated at 180–200° C. under an argon atmosphere for 1 h. After cooling to ambient temperature the reaction mixture was diluted with water (50 ml) and washed with ethyl acetate (2×20 ml). The aqueous layer was basified with ammonia (880) and the product extracted with dichloromethane (3×50 ml). The combined organic material was dried over magnesium sulfate and evaporated. The crude product was crystallized from ethanol (10 ml) to afford yellow solid (0.60 g). $^1$H NMR (300 MHz, $d_6$-DMSO) 12.50 (1H, br s), 8.20 (2H, d), 8.03 (2H, d), 7.93 (1H, s), 7.81 (1H, s).

Step b. 4-(4-Nitro-phenyl)-1-N,N-dimethylsulfamoyl-1-imidazole. To a solution of the product from step a (3.53 g, 20.4 mmol) in dry N,N-dimethylformamide (20 ml), cooled with ice under an atmosphere of argon was added sodium hydride (0.82 g, 20.4 mmol 60% dispersion in oil). The mixture was stirred at room temperature for 1 h, then N;N-dimethylsulfamoyl chloride (2.4 ml, 22.4 mmol) was added and the stirring was continued overnight. Water (400 ml ) was added, and the resulting precipitate was filtered, washed with water, ethanol and diethyl ether and then dried to give the required product (3.96 g). $^1$H NMR (300 MHz, $d_6$-DMSO) 8.49 (1H, s), 8.33 (1H, s), 8.26 (2H, d), 8.15 (2H, d), 2.88 (6H, s).

Step c. 4-(1-N,N-Dimethylsutfamoyl-1H-imidazol-4-yl)-phenylamine. A round bottom flask containing the product from the previous step (3.96 g, 13.4 mmol), 10% palladium-on-charcoal (0.4 g) and tetrahydrofuran:methanol 1:1 (120 ml) was evacuated and flushed with hydrogen three times. The mixture was vigorously stirred overnight under an atmosphere of hydrogen. The catalyst was removed by filtration and the filtrate evaporated to afford a yellow solid (3.41 g): $^1$H NMR (300 MHz, $d_6$-DMSO) 8.09 (1H, s), 7.77 (1H, s), 7.52 (2H, d), 6.56 (2H, d), 5.17 (2H, br s), 2.82 (6H, s).

Step d. C-(4-Chloro-phenyl)-N-[4-(1-N,N-dimethylsuffamoyl-1-imidazol-4-yl)-phenyl]-methanesulfonamide. The product was prepared according to the procedure given in Example 2 step a using the product of step c above instead of the product of Example 1 step c as the amine substrate. $^1$H NMR (300 MHz, $d_6$-DMSO) 9.90 (1H, s), 8.21 (1H, s), 8.08 (1H, s), 7.82 (2H, d), 7.43 (2H, d), 7.26 (2H, d), 7.20 (2H, d), 4.50 (2H, s), 2.85 (6H, s), Step e. The product from the previous step was converted to the hydrochloride salt of the title compound using the procedure given in Example 2 step b. $^1$H NMR (300 MHz, $d_6$-DMSO) 10.13 (1H, s), 9.19 (1H, s), 8.08 (1H, s), 7.83 (2H, d), 7.42 (2H, d), 7.27 (4H, m), 4.57 (2H, s). Found C 49.93, H 3.89, N 10.84%, $C_{16}H_{15}Cl_2N_3O_2S$ requires C 50.01, H 3.94, N 10.94%.

EXAMPLE 6

C-(4-Chloro-phenyl)-N-[3-(1H-imidazol-4-ylmethyl)-benzyl]-methanesulfonamide

Step a. 3-[Hydroxy-(1-trityl-1H-imidazol-4-yl)-methyl]-benzonitrile. The product was prepared according to the procedure given in Example 1 step a using 3-cyanobenzaldehyde-instead of 4-cyanobenzaldehyde. $^1$H NMR (300 MHz, $CDCl_3$) 7.68 (2H, d), 7.52 (1H, s), 7.43 (2H, m), 7.32 (9H, m), 7.12 (6H, m), 6.61 (1H, s), 5.77 (1H, s),3.5 (1H, br s).

Step b. 3-(1-Trityl-1-imidazol-4-ylmethyl)-benzonitrile. The product was prepared according to the procedure given in Example 1 step b using the product of step a above as substrate. $^1$H NMR (300 MHz, $CDCl_3$) 7.47 (3H, m), 7.40 (1H, m), 7.35 (10H, m), 7.14 (6H, m), 6.60 (1H, s), 3.92 (2H, s).

Step c. 3-(1-Trityl-1-imidazol-4-ylmethyl)-benzylamine. The product of step b above was converted to the amine according to the procedure of Example 1 step c. $^1$H NMR (300 MHz, $CDCl_3$) 7.36–7.12 (20H, m), 6.55 (1H, s), 3.89 (2H, s), 3.81 (2H, s).

Step d. C-(4-Chloro-phenyl)-N-[3-(1-trityl-1H-imidazol-4-ylmethyl)-benzyl]-methanesulfonamide. The product was prepared according to the procedure given in Example 2 step a using the product of step c above instead of the product of Example 1 step c as the substrate. $^1$H NMR (300 MHz, $CDCl_3$) 7.31 (13H, m). 7.12 (11H, m), 6.57 (1H, s), 4.63 (1H, t), 4.14 (2H, d), 4.09 (2H, s), 3.88 (2H, s).

Step e. The product from the previous step was converted to the hydrochloride salt of the title compound using the procedure given in Example 2 step b. $^1$H NMR (300 MHz, $d_6$-DMSO) 14.23 (2H, br s), 8.97 (1H, s), 7.66 (1H, t), 7.44–7.15 (9H, m), 4.33 (2H, s), 4.07 (2H, d), 4.02 (2H, s). Found C 49.81, H 4.88, N 9.70%, $C_{18}H_{19}Cl_2N_3O_2S$. 1.2 $H_2O$ requires C 49.88, H 4.96, N 9.70%.

EXAMPLE 7

C-(4-Chloro-phenyl)-N-{2-[4-(1H-imidazol-4-ylmethyl)-phenyl]-ethyl}-methanesulfonamide Step a. (4-Diethoxymethyl-phenyl)-(1-trityl-1H-imidazol-4-yl)-methanol. The product was prepared according to the procedure given in Example 1 step a using terephthaldehyde mono-(diethylacetyl) instead of 4-cyanobenzaldehyde $^1$H NMR (300 MHz, $CDCl_3$) 7.38 (4H, m), 7.31 (10H, m), 7.11 (6H, m), 6.56 (1H, s), 5,77 (1H, s), 5.47 (1H, s), 3.53 (5H, m), 1.23 (6H, m).

Step b. 4-(4-Diethoxymethyl-benzyl)-1-trityl-1-imidazole. The product was prepared according to the procedure given in Example 1 step b using the product of step a above as substrate. $^1$H NMR (300 MHz, CDCl$_3$) 7.32 (14H, m), 7.14 (6H, m), 6.53 (1H, s), 5.46 (1H, s), 3.90 (2H s), 3.54 (4H, m), 1.23 (6H, m).

Step c. 4-(1-Trityl-1H-imidazol-4-ylmethyl)-benzaldehyde. To a solution of the product of step b above (1.24 g, 2.47 mmol) in acetone (15 ml) was added Amberlyst-15 ion-exchange resin (0.15 g) and water (0.2 ml). The reaction was stirred overnight at room temperature, filtered and the resin was washed with additional acetone (25 ml). The filtrate was dried (MgSO$_4$), and evaporated to afford the aldehyde as a white solid (0.63 g). $^1$H NMR (300 MHz, CDCl$_3$) 9.98 (1H, s), 7.80 (2H, d), 7.41 (3H, m), 7.33 (9H, m), 7.14 (6H, m), 6.61 (1H, s), 4.00 (2H, s).

Step d. 4-(1-Trityl-1-imidazol-4-ylmethyl)-phenyl]-acetonitrile. To a solution of t-BuOK in tetrahydrofuran (4.6 ml of a 1M solution) at −40 °C. was added the solution of tosylmethyl isocyanide (TosMic) (0.52 g, 2.65 mmol) in tetrahydrofuran (5 ml), then the solution of the product of step c above (0.96 g, 2.20 mmol) in tetrahydrofuran (5 ml). After 1 h stirring at −40° C. methanol (10 ml) was added and the reaction was heated at reflux for 20 min. The reaction mixture was cooled to room temperature and the solvent was evaporated under reduced pressure. The residue was dissolved in dichloromethane (20 ml) and washed with water/acetic acid (10 ml/0.4 ml). The aqueous layer was extracted with dichloromethane (2×10 ml) and the combined organic layers were washed with saturated sodium hydrogen carbonate, dried (MgSO$_4$) and the solvent was evaporated. Flash column chromatography (silica; hexane:isopropanol 85:15) of the residue afforded the product as a white solid (0.42 g). $^1$H NMR (300 MHz, CDCl$_3$) 7.38–7.12 (20H, m), 6.56 (1H, s), 3.89 (2H, s), 3.69 (2H, s).

Step e. 2-[4-(1-Trityl-1H-imidazol-4-ylmethyl)-phenyl]-ethylarnitle. The product of step d above was converted to the amine according to the procedure of Example 1 step c. $^1$H NMR (300MHz, CDCl$_3$) 7.33 (10H, m), 7.13 (10H, m), 6.56 (1H, s), 3.87 (2H, s), 2.94 (2H, t), 2.71 (2H, t).

Step f. C-(4-Chloro-phenyl)-N-{2-[4-(1-trizyl-1H-imidazol-4-ylmethyl)-phenyl]-ethyl}-methanesulfonamide. The product was prepared according to the procedure given in Example 2 step a using the product of step e above instead of the product of Example 1 step c as the substrate. $^1$H NMR (300 MHz, CDCl$_3$) 7.28 (12H, m), 7.14 (10H, m), 7.05 (2H, d), 6.58 (1H, s), 4.12 (1H, t), 4.09 (2H, s), 3.88 (2H, s), 3.21 (2H, dd), 2.74 (2H, t).

Step g. The product from the previous step was converted to the hydrochloride salt of the title compound using the procedure given in Example 2 step b. $^1$H NMR (300 MHz, d$_6$-DMSO) 14.34 (2H, br s), 8.96 (1H, s), 7.40 (3H, m), 7.33 (2H, d), 7.18 (5H, m), 4.30 (2H, s), 3.98 (2H, s), 3.07 (2H, q), 2.68 (2H, t). Found C 51.44, H 5.03, N 9.27%; C$_{19}$H$_{21}$Cl$_2$N$_3$O$_2$S. 1.0 H$_2$O requires C 51.38, H 5.21, N 9.46%.

REFERENCES

1. R. M. Turner, S. D. Lindell *J. Org. Chem.* 1991, 56, 5739
2. R. C. Vollinga, W. M. P. B. Menge, R. Leurs, H. Timmerman *J. Med Chem.* 1995, 38, 266.

The biological activity of the compounds of the examples was measured using the ileal longitudinal muscle, myenteric plexus assay described by Paton and Aboo Zar (*J. Physiol.* 1968, 194, 13–33). Male Dunkin-Hartley guinea pigs (250–300 g) were employed. Briefly, a 50 cm portion of ileum proximal to the caecum was removed, after discarding the terminal 20 cm. Ileal segments (3 cm) were cleaned by passing Krebs-Henseleit buffer containing 3 µM mepyramine gently through the ileum using a Pasteur pipette (size: 13.8 cm length, 0.65 cm diameter). To avoid unnecessary damage to the tissue, Krebs-Henseleit buffer was passed through the ileal segment, while it was lying horizontally on a petri dish. Therefore, the ileum was not over-distended and the buffer flowed through with ease. Each segment was then passed over a Pasteur pipette and the longitudinal muscle layer and adhering myenteric plexus was teased away using moist cotton wool, by stroking tangentially away from the mesenteric attachment. The tissues were suspended in 20 ml organ baths containing Krebs-Henseleit buffer at 37±1° C. and gassed with 95% CO$_2$/5% O$_2$. The tissues were ligated to two parallel stainless steel wires, situated between two platinum electrodes (0.76 cm length, 0.06 cm diameter). All measurements were recorded isometrically (Grass FTO3 transducer). Following an initial loading tension of 1 g, the tissues were stimulated with electrical pulses at a frequency of 0.1 Hz and a pulse duration of 0.5 msec, as described by Kosterlitz & Watt (*Br. J. Pharmacol.* 1968, 266–276). Initially, the tissues were stimulated at supramaximal (1.3 fold times maximal) voltage for a period of 30 min and then the tissues were washed and re-stimulated. A "sighter dose" of the selective histamine H$_3$-receptor agonist, R-(α)-methylhistamine (0.3 µM) (Arrang et al. *Nature*, 1987, 117–123), was administered. Upon generation of response, the "sighter dose" was removed from the tissues by "washout" (6 washes over 60 min) and during this period the electrical stimulation was switched off. The tissues were then re-stimulated and allowed to stabilise prior to the addition of drug treatments, which were allocated on a randomised block basis to the organ baths. Following the incubation period, a single cumulative E/[A] curve was obtained. The experimental E/[A] curve data was expressed as the percentage inhibition of the peak height of electrically-stimulated contraction. Antagonist affinity values were calculated from the degree of rightward shift of the R-(α)-methylhistamine E/[A] curves using Schild's methods (Arunlakshana & Schild Br. *J. Pharmacol.* 1959, 48–58). The results are set out in Table 1. Typical variance in this assay is ±0.15 log units.

TABLE 1

| Example No. | pK$_B$ (functional assay) - ileum |
| --- | --- |
| 1 | 6.64 |
| 2 | 7.15 |
| 3 | 6.95 |
| 4 | 6.39 |
| 7 | 6.02 |

Histamine H$_3$ Radioligand Binding Assay—Guinea Pig Ileum

Preparation of Membranes

Male Dunkin Hartley guinea pigs (200–300 g) were used. The small intestine was rapidly removed (cut ~5 cm from caecum and 5 cm from stomach) and placed in ice-cold 20 mM Hepes-NaOH buffer (pH7.4 at 21±3° C.). The tissue was cut into ~10 cm segments, flushed through with ice-cold 20 mM Hepes-NaOH buffer and placed in a beaker containing fresh buffer at 4° C. 10 cm segments of ileum were threaded onto a glass pipette and the longitudinal muscle myenteric plexus was peeled away from the circular muscle using damp cotton-wool. Longitudinal muscle myenteric plexus was immediately placed in ice-cold Viaspan® solution (~100 ml for tissue from 3 guinea pigs) and placed in the refrigerator for 24 hours.

Pre-soaked tissue was weighed and minced with scissors. The tissue was then homogenised in VIASPAN® (BELZER UW) using a polytron (Kinematica AG; PT-DA 3020/2TS, 3×~1–2s). 50 ml of 500 mM Tris HCl (pH 6.9 at 21±3° C.) was added to the tissue and the mixture centrifuged at 39,800×g for 12 min at 4° C. The supernatant was discarded and rehomogenised in 100 ml ice-cold 20 mM Hepes-NaOH buffer (pH7.4 at 21±3° C.) using a teflon-in-glass homogeniser (setting 10;3×). The homogenate was recentrifuged at 39, 800×g and the pellet resuspended in 20 mM Hepes-NaOH buffer (pH 7.4 at 21±3° C.), to a tissue concentration of 50 mg.ml$^{-1}$, using a polytron (Brinkman, PT10, 3×1s).

Incubation Conditions

Guinea pig ileum longitudinal muscle myenteric plexus membranes (400µl) were incubated for 165 min at 21±3° C. in a final volume of 500 µl with 20 mM Hepes-NaOH buffer containing [$^3$H]-R-α-methylhistamine (50 µl; 3 nM) and competing compound. Total and non-specific binding of [$^3$H]-R-α-methylhistamine were defined using 50 µl of buffer and 50 µl of 10 µM thioperamide, respectively. The assay was terminated by rapid filtration through Whatman GF/B filters, presoaked (2 hr) in 0.1% polyethyleneimine, using a Brandell Cell Harvester. The filters were washed (3×3 ml) with ice-cold 50 mM Tris-HCl (pH6.9 at 21±3° C.), transferred into scintillation vials, 5 ml liquid scintillation cocktail was added and after 4 hours the bound radioactivity was determined by counting (4 min) in a Beckman liquid scintillation counter.

Data Anlysis

Data are analysed using GraphPad prism and the general equation for a competition curve with variable Hill slope ($n_H$).

$$Y = \text{Non-specific binding} + \frac{(\text{Total binding} - \text{Non-specific binding})}{1 + 10^{((\log IC_{50} - X)n_H)}}$$

where

X is the log concentration of competing compound,

Y is the binding obtained at each concentration of X, pIC$_{50}$ is the concentration of the competitor required to compete for half of the specific binding.

The IC$_{50}$ is converted to the K$_i$ using the Cheng Prusoff equation, $$K_I = IC_{50}/(1+(L/K_D))$$

where

IC$_{50}$ is the concentration of competitor required to compete for half the specific binding, L is the radioligand concentration used, K$_D$ is the equilibrium dissociation constant for the radioligand determined by saturation experiments.

The results are set out in Table 2. Typical variance in this binding assay is 0.12 log units.

TABLE 2

| Example No. | pK$_I$ (binding assay) - ileum |
|---|---|
| 1 | 6.47 |
| 2 | 6.85 |

Histamine H$_3$ Radioligand Binding Assay—Guinea Pig Cortex

Preparation of Membranes

Male Dunkin Hartley guinea pigs (200–300 g) were used. The whole brain was removed and immediately placed in ice-cold 20 mM Hepes-NaOH buffer (pH7.4 at 21±3° C.). The cortex was dissected, weighed and homogenised in ice-cold 20 mM Hepes-NaOH buffer (pH7.4 at 21±3° C.) (50 ml/guinea-pig cortex) using a polytron (Kinematica AG, PT-DA 3020/2TS, 3×3s). The homogenate was centrifuged at 100×g for 5 min and the supernatants pooled and stored at 4° C. The pellets were rehomogenised in fresh ice-cold buffer (80 ml) and recentrifuged (100×g for 5 min). The supernatants were pooled and pellets rehomogenised and recentrifuged (100×g for 5 min). All supernatants were pooled and centrifuged at 39,800×g for 12 min at 4° C. The final pellet was resuspended in 20 mM Hepes-NaOH buffer (pH7.4 at 21±3° C.) to a tissue concentration of 7.5 mg.ml$^{-1}$, using a teflon-in-glass homogeniser.

Incubation Conditions and Data Analysis

These were essentially identical to those used for the guinea pig ileum myenteric plexus assay described above, except that the final assay concentration of [$^3$H]-R-α-methylhistamine was 0.1 nM. The results are set out in Table 3. Typical variance in this binding assay is ±0.12 log units.

TABLE 3

| Example No. | pK$_I$ (binding assay) - cortex |
|---|---|
| 1 | 6.49 |
| 2 | 7.54 |
| 3 | 7.80 |
| 4 | 7.03 |
| 5 | 5.85 |
| 6 | 6.43 |
| 7 | 6.54 |

What is claimed is:

1. A compound of the formula wherein R$^1$ is selected from C$_1$ to C$_6$ alkyl, C$_1$ to C$_6$ alkoxy, C$_1$ to C$_6$ alkylthio, carboxy, carboxy(C$_1$ to C$_6$)alkyl, formyl, C$_1$ to C$_6$ alkylcarbonyl, C$_1$ to C$_6$ alkylcarbonylalkoxy, nitro, trihalomethyl, hydroxy, amino, C$_1$ to C$_6$ alkylamino, di(C$_1$ to C$_6$ alkyl)amino, aryl, C$_1$ to C$_6$ alkylaryl, halo, sulfamoyl and cyano;

R$^2$ represents a bond or C$_1$ to C$_5$ hydrocarbylene;

R$^3$ is selected from the groups recited above for R$^1$;

R$^4$ represents a bond or C$_1$ to C$_5$ hydrocarbylene;

$R^5$ is hydrogen, $C_1$ to $C_3$ alkyl, $R^8$—O—($C_1$ to $C_3$)alkyl (wherein $R^8$ is hydrogen or $C_1$ to $C_3$ alkyl), aryl, aryl($C_1$ to $C_3$)alkyl or heterocyclic($C_1$ to $C_3$)alkyl;

$R^6$ represents a bond or —$NR^9$—, wherein $R^9$ is any of the groups recited above for $R^5$;

$R^7$ is cycloalkyl($C_1$ to $C_3$ alkyl), phenyl ($C_1$ to $C_3$ alkyl), naphthyl or naphthyl($C_1$ to $C_3$)alkyl, optionally substituted by $C_1$ to $C_6$ alkyl, $C_1$ to $C_6$ alkoxy, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, amino, $C_1$ to $C_6$ alkylamino, di($C_1$ to $C_6$ alkyl)amino, halo, sulfamoyl or cyano;

a is from 0 to 2; and b is from 0 to 3;

or a pharmaceutically acceptable salt thereof.

2. A compound according to claim 1 wherein a=0.

3. A compound according to claim 1 wherein b=0.

4. A compound according to claim 1 wherein $R^5$ is hydrogen, $C_1$ to $C_3$ alkyl, or $R^8$—O—($C_1$ to $C_3$)alkyl (wherein $R^8$ is hydrogen or $C_1$ to $C_3$ alkyl).

5. A compound according to claim 1 wherein $R^9$ is hydrogen, $C_1$ to $C_3$ alkyl, or $R^8$—O—($C_1$ to $C_3$)alkyl (wherein $R^8$ is hydrogen or $C_1$ to $C_3$ alkyl).

6. A compound according to claim 1 wherein $R^2$ is a bond or $C_1$ to $C_3$ hydrocarbylene.

7. A compound according to claim 1 wherein $R^4$ is a bond or $C_1$ to $C_3$ hydrocarbylene.

8. The compound of claim 1, wherein $R^2$ represents $C_1$ to $C_3$ hydrocarbylene.

9. The compound of claim 1, wherein $R^4$ represents $C_1$ to $C_3$ hydrocarbylene.

10. A pharmaceutical composition comprising a therapeutically effective amount of a compound according to claim 1, and a physiologically acceptable diluent or carrier.

11. A method of treating hypersensitive bodily reactions in a patient, comprising administering to said patient an effective amount of a compound of claim 1.

12. The method of claim 11, wherein said hypersensitive reaction is an allergic rash, hayfever or asthma.

13. A method of treating disorders associated with excessive levels of histamine in a patient, comprising administering to said patient an effective anti-histamine amount of a compound of claim 1.

14. The method of claim 13, wherein said disorder is selected from the group consisting of an allergic rash, hayfever, asthma, sleeplessness, convulsion, depression, poor cerebral circulation and irritable bowel syndrome.

15. A method of making a compound according to claim 1 wherein $R^6$ is a bond, said method comprising the step of reacting a compound of formula with a sulfonyl chloride of formula $R^7SO_2Cl$, wherein $R^1$, $R^2$, $R^3$, $R^4$, $R^5$, $R^7$, a and b are as defined in claim 1, and Z is a suitable protecting group.

16. A method of making a compound according to claim 1 wherein $R^6$ is —$NR^9$—, said method comprising the step of reacting a compound of formula with a) sodium hydride, and then with a compound of formula $R^7Br$, or b) a compound of formula $R^7OH$, wherein $R^1$, $R^2$, $R^3$, $R^4$, $R^5$, $R^7$, $R^9$, a and b are as defined in claim 1, and Z and Z' are suitable protecting groups.

17. A method of making a compound according to claim 1 wherein $R^6$ is —$NR^9$—, said method comprising the step of reacting a compound of formula with a) sodium hydride, and then with a compound of formula or b) a compound of formula wherein $R^1$, $R^2$, $R^3$, $R^4$, $R^5$, $R^7$, $R^9$, a and b are as defined in claim 1, and Z and Z' are suitable protecting groups.

* * * * *